United States Patent [19]
Pierce

[11] Patent Number: 5,392,808
[45] Date of Patent: Feb. 28, 1995

[54] RETRACTABLE TUBING REEL

[76] Inventor: Elton J. Pierce, 124 Wilmington, Clovis, N. Mex. 88101

[21] Appl. No.: 276,207

[22] Filed: Jul. 18, 1994

[51] Int. Cl.⁶ .............................................. B65H 75/34
[52] U.S. Cl. ................................. 137/355.23; 242/385
[58] Field of Search ........... 137/355.2, 355.21, 355.23, 137/355.16; 242/382, 382.5, 385

[56] References Cited

U.S. PATENT DOCUMENTS

| | | |
|---|---|---|
| 1,537,637 | 5/1925 | Jarvis . |
| 2,286,904 | 6/1942 | Ewald . |
| 2,401,809 | 6/1946 | Ziegler . |
| 2,533,432 | 12/1950 | Clark . |
| 2,707,467 | 5/1955 | Pelzer et al. . |
| 2,907,534 | 10/1959 | Benstein ..................... 137/355.23 X |
| 3,612,094 | 10/1971 | Hare ................................ 137/355.2 |
| 3,854,017 | 12/1974 | Crim ............................ 137/355.23 X |
| 4,010,913 | 3/1977 | Guerster et al. . |
| 4,151,648 | 5/1979 | Hirth . |
| 4,446,884 | 5/1984 | Rader, Jr. ....................... 137/355.23 |
| 4,543,982 | 10/1985 | Wolfe . |
| 4,719,991 | 1/1988 | Diehn et al. . |
| 5,236,143 | 8/1993 | Dragon . |

Primary Examiner—Martin P. Schwadron
Assistant Examiner—Kevin L. Lee
Attorney, Agent, or Firm—Novak, Vickers & Burt

[57] ABSTRACT

A retractable tubing reel device utilized in conjunction with a oxygen supply tank and nasal oxygen catheter, the device having an extended length of tubing allowing a patient greater movement beyond the immediate area of the oxygen tank, the device having a mechanism for retracting any excess extended tubing thereby preventing constriction and tangling of the tubing. The device retracting the tubing into a housing where the tubing is rewound in a manner which also prevents constriction and tangling of the tubing inside the housing. The device constructed for facilitated servicing of the tubing through easy removal of the coiled tubing from the housing of the device.

18 Claims, 3 Drawing Sheets

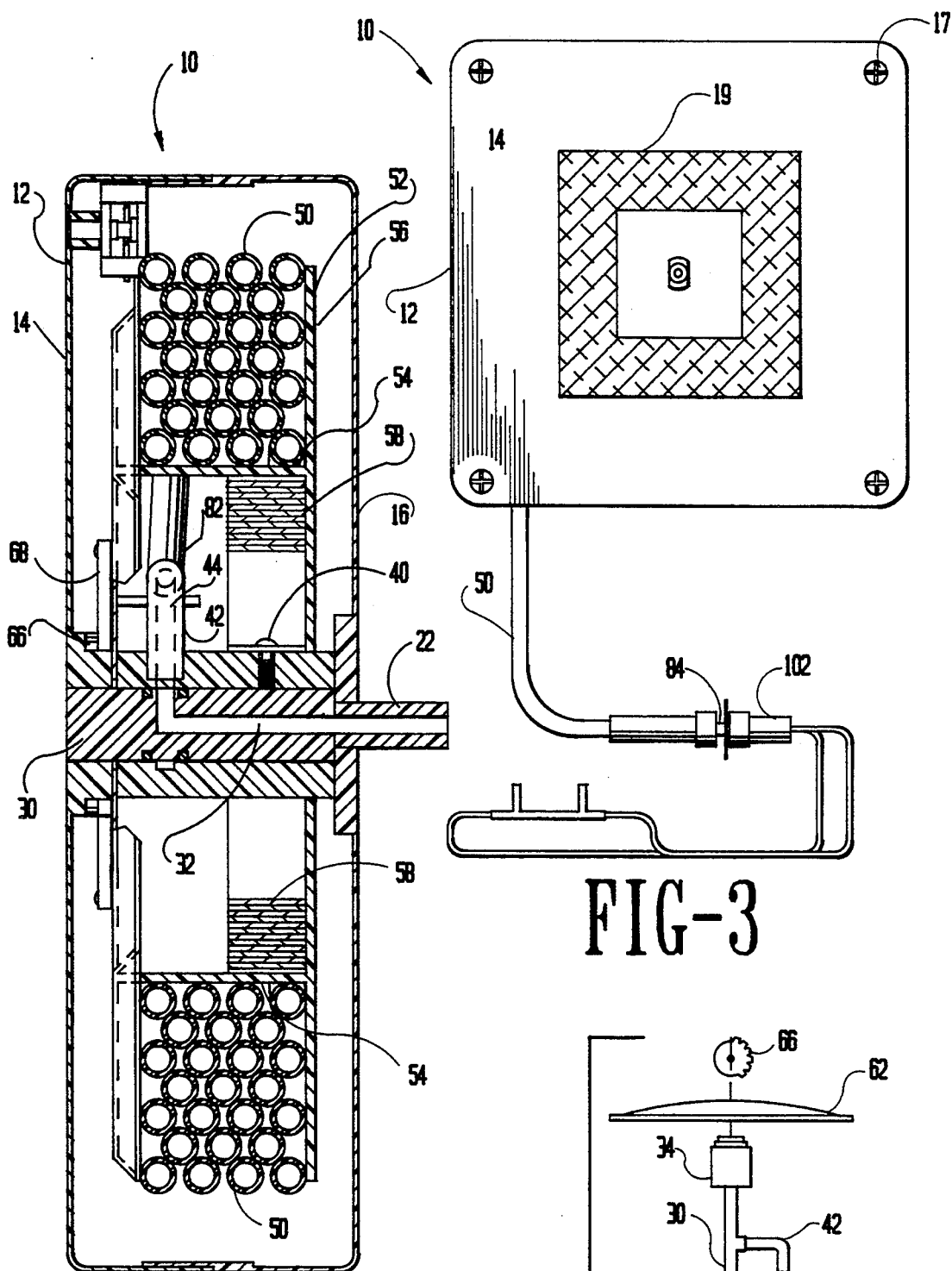

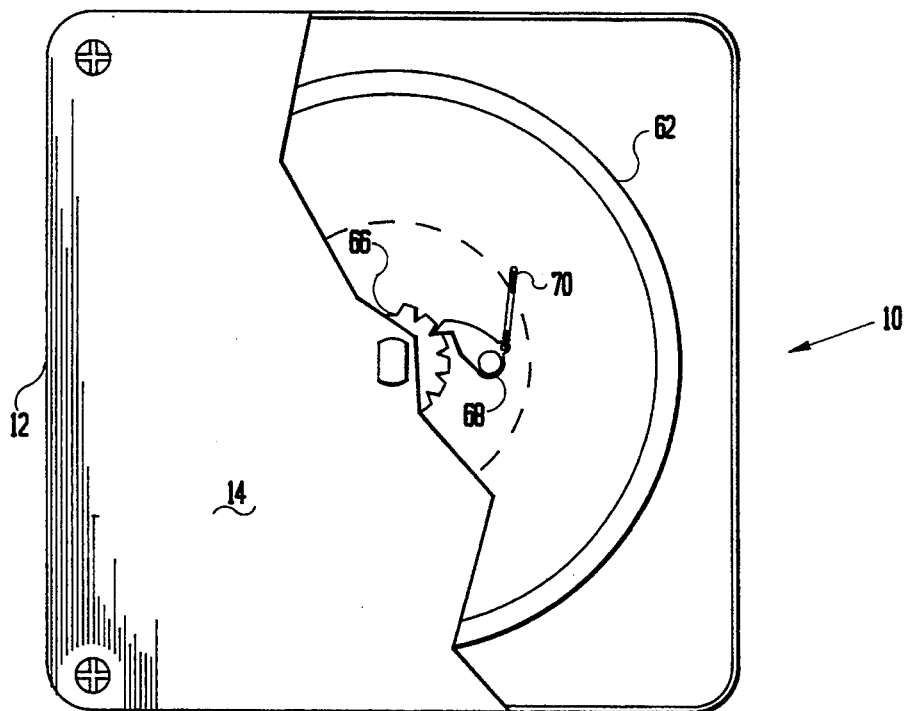
FIG-5
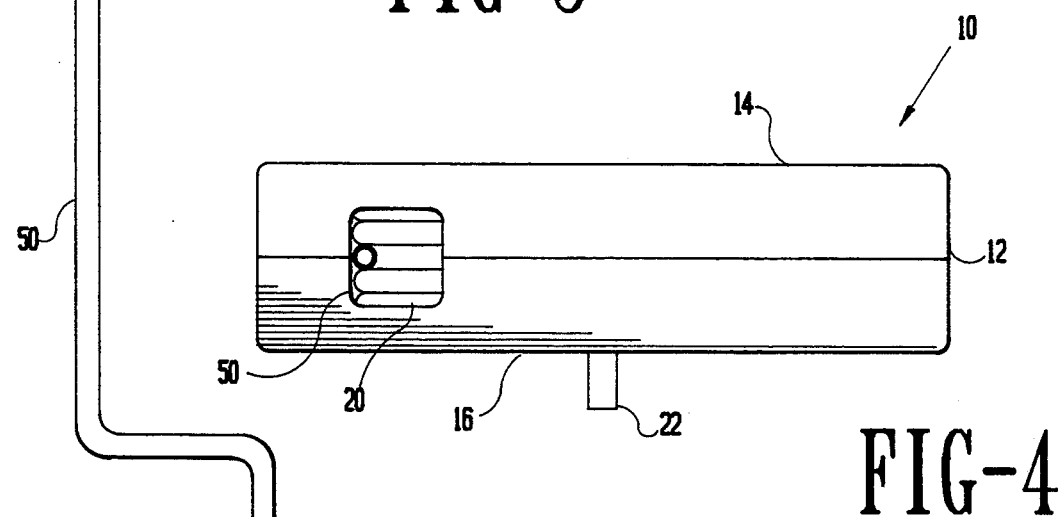
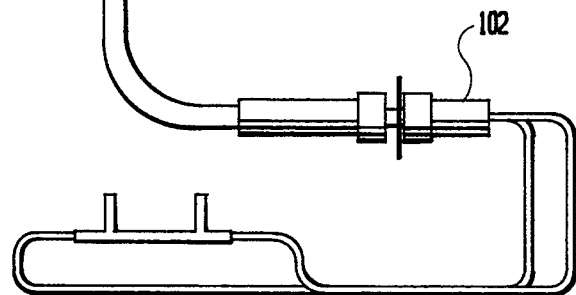
FIG-4

RETRACTABLE TUBING REEL

BACKGROUND OF THE INVENTION

1) Field of the Invention

The present invention relates generally to retractable tubing reels, and more particularly to a retractable tubing reel for supplying oxygen to a patient.

2) Description of the Related Art

Hospitalization sometimes requires that a patient receive oxygen therapy for the treatment of conditions resulting from oxygen deficiency. Oxygen therapy is used to combat acute arterial anoxia that may result from pneumonia, pulmonary edema, or obstruction to breathing. Oxygen therapy is also employed in congestive heart failure, coronary thrombosis, and following surgery. Oxygen therapy may be administered by nasal catheter, mask, funnel, oxygen tent, or special oxygen chamber, and usually in a concentration of seventy to one hundred percent. One of the most common methods of administering oxygen therapy is through nasal catheter to allow the patient the ability to move about normally and with less intrusions. The nasal catheter is connected to a stationary oxygen supply unit such as a tank, through tubing connected between the catheter and the stationary oxygen tank.

A patient undergoing oxygen therapy has limited movement due to the need to be close to a stationary oxygen supply unit. If a long tubing was connected between the stationary supply unit and the nasal catheter, the patient would have to worry about tangling and pinching of the tubing which would result in the oxygen being constricted and unavailable for the patient. Also, if excess tubing were to lay on a cold floor for any amount of time, condensation would commence in the tubing creating problems for the patient. What is needed is a means for allowing a patient undergoing oxygen therapy, or some other gas therapy, to freely move about a large area from a stationary gas supply unit. The oxygen, or gas, supplied to the patient must not be constricted or the flow to the patient reduced, and an indisposed patient must be able to use this means without exerting themselves. Some prior inventions have retraction mechanisms, however, these inventions are incompatible with oxygen therapy devices. Another problem associated with oxygen therapy is the necessity to easily service the tubing. The oxygen tubing must be removed for cleansing and sterilization on a regular maintenance schedule. Any device providing extra tubing must allow for facilitated servicing of that extra tubing, especially in a hospital where there might be hundreds of oxygen tubing that needs servicing.

Dragon, U.S. Pat. No. 5,236,143, discloses an intravenous tubing retractor apparatus including a container with a feed conduit, a retraction means with a spool, a pair of guide rollers, and a mounting boss with "L" shaped pivot arms.

Nederman, U.S. Pat. No. 4,224,960, discloses a wind-up device for flexible conduits comprising a drum in which a flexible conduit is enclosed, a stationary shaft, a coil spring assembly, a fixation element for effecting tensioning or release of the coil spring, the coil spring capable of rapid replacement without any need of releasing internal parts.

Guerster et al, U.S. Pat. No. 4,010,913, discloses a retriever reel for electrical or fluid lines comprising a stationary base, a drum, a continuous line, a spring, and a pair of clamps, the reel departing from the use of expensive slip rings or rotary joints.

SUMMARY OF THE INVENTION

The present invention is a device for allowing a patient undergoing oxygen therapy, or any other gas therapy, greater movement around a large area from a stationary oxygen supply unit. The patient is also relieved of the worry of tangling or pinching of their tubing because the excess tubing of the present invention can easily be retracted into a housing until further need arises for more tubing. The present invention also provides for facilitated servicing of the tubing without having to uncoil the tubing from the device.

The retractable tubing reel device of the present invention is utilized in conjunction with a stationary gas supply, such as a oxygen tank, and a patient intake unit such as a nasal catheter. The device consist of an attachable housing, an inlet flow conduit, a central swivel shaft, an extension unit, a flexible flow conduit, a gear assembly and a spring assembly.

The attachable housing, which encloses most of the other components of the device in a protective shell, has an attachment casing member and an inlet casing member which are essentially symmetrical in shape and mated to each other to form the attachable housing. In the preferred embodiment, the attachable casing member is connected to the inlet casing member by four countersunk bolts which are easily removable for facilitated servicing of the device. The attachment casing member has a means for attachment to a base unit, the means for attachment in one embodiment being velcro. The inlet casing member has an inlet aperture in order to place the inlet flow conduit therethrough. The attachable housing has a conduit aperture for allowing ingress and egress of the flexible flow conduit. In the preferred embodiment, the attachable housing is composed of a resilient material, such as a hard plastic material, in order to protect the flexible flow conduit coiled in its interior.

The inlet flow conduit has an exterior end and an interior end and is a means for transferring oxygen, or some other gas, from a stationary gas supply to the device. In the preferred embodiment, the inlet flow conduit is a plastic tubing conducive to the transfer of oxygen. The exterior end of the inlet flow conduit is connected to the release valve of the stationary gas supply, and the interior end is placed therethrough the inlet aperture and connected to the central swivel shaft.

The central swivel shaft has a gear end and spring end, and is enclosed within the attachable housing. The central swivel shaft is essentially cylindrical in shape and is positioned at a horizontal axis across the attachable housing. The central swivel shaft has a central passageway for the flow of gas which is in flow communication with the inlet flow conduit and an extension passageway of the extension unit. The central swivel shaft act as a base for the other components of the device enclosed within the attachable housing.

The extension unit has a swivel end and a conduit end, and is connected perpendicular to the central swivel shaft, at its swivel end. The extension unit is connected to the middle of the central swivel shaft. The extension unit has an extension passageway therethrough which is in flow communication with the central passageway and the flexible flow conduit which is connected to the conduit end of the extension unit. The novel extension unit is capable of 180 degree movement in order to prevent tangling and miscoiling of the flexible flow conduit.

The flexible flow conduit has an inlet end and an outlet end, and is attached to the extension unit at its inlet end and through the conduit aperture of the attachable housing to a patient's gas intake unit at its outlet end. In the preferred embodiment, the flexible flow conduit is a plastic tubing conducive to transferring oxygen. The flexible flow conduit is wound around the spring reel during its coil state when there is no need for extension of the flexible flow conduit by the patient. When the patient departs from the stationary gas supply, the flexible flow conduit is extended from the attachable housing in order to provide the patient with the freedom to move about while still receiving gas from the stationary gas supply. When the patient moves toward the stationary gas supply, the flexible flow conduit is retracted by slightly tugging on it which recoils any excess flexible flow conduit. Recoiling of the flexible flow conduit prevents tangling and constriction of the conduit, and also prevents condensation build up in the conduit. During servicing of the flexible flow conduit, the inlet end is easily uncoupled from the extension unit, and the outlet end easily uncoupled from the patient gas intake unit. The coiled flexible flow conduit can then be removed for maintenance, and a new coiled flexible flow conduit installed in its place.

The gear assembly is enclosed within the attachable housing, and consists of a gear reel, a gear catch lever, a half gear, and a gear compression spring. The gear reel is circular in shape and has a central aperture for engagement with the gear end of the central swivel shaft. The gear reel rotates reciprocally with the spring reel and forms a boundary for the flexible flow conduit. The gear catch lever is mounted to the gear reel and engages the half gear which is mounted to the gear end of the central swivel shaft. The gear compression spring is attached to the gear catch lever and assist in the engagement with the half gear. The half gear engages the gear catch lever during extension of the flexible flow conduit, and disengages the half gear during retraction of the flexible flow conduit.

The spring assembly is enclosed within the attachable housing and consists of a spring reel and a tension spring. The spring reel has a flat circular portion and a rim-like cylindrical portion perpendicular to the circular portion. The circular portion forms a second boundary for the flexible flow conduit opposite the boundary formed by the gear reel. The cylindrical portion is attached to the gear reel through a plurality of reel couplings. The spring reel has a central cavity in which the central swivel shaft is extended therethrough and engaged with the spring reel at the spring end of the central swivel shaft. The tension spring is connected to the central swivel shaft at a spring catch, both the tension spring and central swivel shaft enclosed by the cylindrical portion of the spring reel. The flexible flow conduit is wound around the perimeter of the cylindrical portion. The spring reel rotates in a first direction when the flexible flow conduit is extended, and in an opposite direction when the flexible flow conduit is retracted. The extension and retraction of the conduit controls the rotation of the spring reel and the gear reel around the stationary central shaft. In the preferred embodiment, the flexible flow conduit is approximately fifteen meters in length.

The present device is constructed to allow for facilitated maintenance of the tubing. The attachable casing member is attached to the inlet casing member by four countersunk bolts which allow for easy removal of the attachable casing member. Once the attachable casing member is removed, the flexible flow conduit can be uncoupled from the extension unit and removed from the housing without having to uncoil it. A new coiled flexible flow conduit can be installed and the attachable casing member reconnected to the inlet casing member, allowing for facilitated servicing of the device. This novel servicing feature of the present invention is beneficial in a hospital situation where tens, or even hundreds of tubing must undergo maintenance on a regular basis.

It is an object of the present invention to provide an improved retractable tubing reel.

It is a further object of the present invention to provide a device which retracts extraneous tubing.

It is a further object of the present invention to provide a device which allows a oxygen supply to be maintained in a separate room away from the patient.

It is a further object of the present invention to provide a device which reduces condensation in oxygen tubing.

It is a further object of the present invention to provide a device which allows for facilitated servicing of oxygen tubing.

BRIEF DESCRIPTION OF THE DRAWINGS

The present invention is further described in connection with the accompanying drawings, in which:

FIG. 1 is a drawing illustrating a side perspective view of the interior of the present invention.

FIG. 2 is a drawing illustrating an exploded view of the interior components of the present invention.

FIG. 3 is a drawing illustrating a side perspective view of the exterior of the present invention.

FIG. 4 is a drawing illustrating a bottom perspective view of the exterior of the present invention.

FIG. 5 is a drawing illustrating a side perspective view of the interior of the present invention.

DETAILED DESCRIPTION OF THE INVENTION

Figure 6:
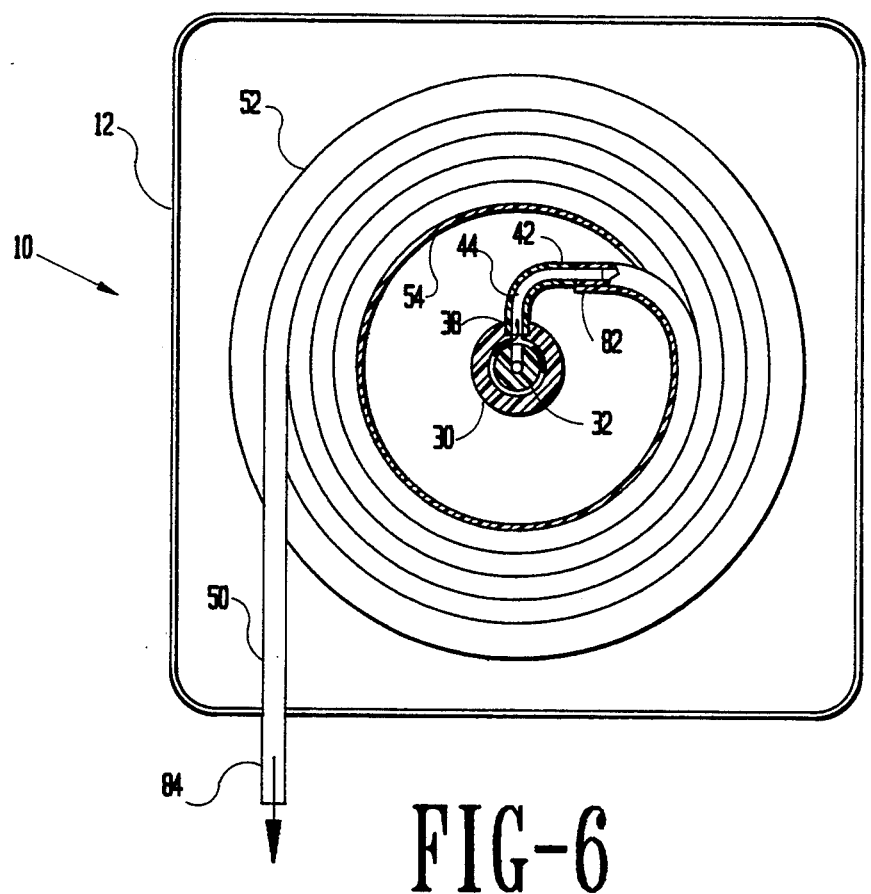
FIG. 6 is a drawing illustrating a side perspective view of the interior of the present invention.

In FIG. 1, the device 10 has an attachable housing 12 consisting of an attachment casing member 14 and an inlet casing member 16. Casing members 14 and 16 are essentially symmetrical in shape and are mated to each other to form attachable housing 12. In the preferred embodiment, members 14 and 16 are connected to each other through a plurality of countersunk bolts 17. Removal of the plurality of countersunk bolts 17 allows for facilitated servicing of the device 10. In the preferred embodiment housing 12 is composed of a resilient material, such as a hard plastic material, to prevent damage to the other components of the device 10. In the preferred embodiment housing 12 forms a cylindrical protective shell around the other components of the device 10 which are enclosed within housing 10. Inlet casing member 16 has an inlet aperture 18 for placement of an inlet flow conduit 22 therethrough. Inlet flow conduit 22 has an interior end 24 and an exterior end 26, not shown, exterior end 26 attached to and in flow communication with a stationary gas supply 28, not shown. Stationary gas supply 28 can be a stationary oxygen supply tank, or a stationary supply tank for other medicinal gases. Inlet flow conduit 22 is coupled to the flow valve of stationary gas supply 28 allowing for flow of the gas from supply 28 to device 10. Interior end 24 is attached a central swivel shaft 30 in the interior of housing 12. In the preferred embodiment, inlet flow conduit 22 is composed of a plastic tubing conducive to transferring of oxygen.

Central swivel shaft 30 is extended across a horizontal axis of housing 12, perpendicular to the faces of casing members 14 and 16. Central swivel shaft 30 is cylindrical shape, having a gear end 34 placed at the interior face of attachment casing member 14, and spring end 36 opposite gear end 34. Central swivel shaft 30 has a central passageway 32 extending from spring end 36 to a middle aperture 38. At spring end 36, inlet flow conduit 22 is coupled to shaft 30 allowing for flow communication between inlet flow conduit 22 and central passageway 32. Central swivel shaft 30 acts as a base for many of the other components of device 10 enclosed within housing 12. Shaft 30 is stationary about the horizontal axis of housing 12.

Extension unit 42 has a swivel end 44 and conduit end 46, and is attached at its swivel end 44 to shaft 30 at middle aperture 38. Extension unit 42 is cylindrical having an extension passageway 48 therethrough, opened at both ends 44 and 46. Extension unit 42 is capable of rotating 180 degrees in order to prevent tangling and constriction of flexible flow conduit 50 while conduit 50 is within housing 12. Extension passage way 48 is in flow communication with central passageway 32 and flexible flow conduit 50 which is attached to extension unit 42 at conduit end 46. In this manner, gas from stationary gas supply 28 is transferred from inlet flow conduit 22, to central passageway 32, to extension passageway 48, and to flexible flow conduit 50.

Flexible flow conduit 50 is an extended length tubing for allowing a patient to move about a large area away from stationary gas supply 28 while safely and effectively transferring gas to the patient. In the preferred embodiment, conduit 50 is a plastic tubing conducive to the transfer of oxygen. Conduit 50 is wound in a coil inside housing 12 during a coil state. During an extension state, conduit 50 is extended beyond housing 12 through conduit aperture 20, not shown. During a retraction state, conduit 50 is recoiled into housing 12. Conduit 50 has an inlet end 82 coupled to the extension unit 42 and an outlet end 84, not shown, coupled to a patient gas intake unit 102, not shown. During servicing, the coiled conduit 50 can be easily uncoupled from the extension unit 42 and the intake unit 102, and removed from housing 12 when casing member 14 is removed. A new coiled conduit 50 can be easily installed and casing member 14 reconnected. The ability to service the device without having to uncoil conduit 50 allows for substantial time saving on behalf of the service company.

Spring reel 52 consists of a cylindrical portion 54 and a flat circular portion 56. Conduit 50 is wound around cylindrical portion 54 of spring reel 52. Flat circular portion 56 of spring reel 52 forms an outer boundary for conduit 50, preventing tangling and constriction of conduit 50 while conduit 50 is wound around cylindrical portion 54. A gear reel 62 forms another outer boundary for conduit 50 opposite flat circular portion 56. Spring reel 52 and gear reel 62 are mounted on and rotate about shaft 30. Gear reel 62 rotates reciprocally with spring reel 52.

FIG. 2 is a drawing illustrating an exploded view of the interior components of the present invention. Referring to FIG. 2, central swivel shaft 30 has gear end 34 and spring end 36 with extension unit 42 perpendicular to shaft 30, attached above middle aperture 38. Tension spring 58 is placed around shaft 30 and attached at spring catch 40. Tension spring 58 is also attached to spring reel 52. Tension spring 58 tightens during the extension state of conduit 50 building up potential energy to be transformed into kinetic energy to recoil conduit 50 during the retraction state. Spring reel 52 is mounted on shaft 30 at spring end 36, cylindrical portion 54 encircling most of shaft 30. Inlet flow conduit 22 is attached at spring end 36 allowing for flow communication between conduit 22 and central passageway 32. On the opposite end of shaft 30, gear reel 62 is mounted on shaft 30 at gear end 34, and connected to spring reel 52 by a plurality of couplings 53, not shown. Half gear 66 is also mounted on shaft 30 at gear end 34.

There is illustrated in FIG. 3 a side perspective view of the exterior of the present invention. Referring to FIG. 3, attachment casing member 14 of housing 12 has conduit aperture 20, not shown, for allowing extension of flexible flow conduit 50 therethrough. Attachment casing member 14 has attachment means 19 on its exterior face. In the preferred embodiment, attachment means 19 is straps of velcro adhesively attached to the exterior face of attachment casing member 14. Plurality of countersunk bolts 17 are placed therethrough casing member 14 and coupled to inlet casing member 16, not shown. In the preferred embodiment, plurality of countersunk bolts 17 are located at the corners of casing member 14 to provide for thorough connection of casing members 14 and 16. Conduit 50 is coupled at outlet end 84 to a patients gas intake unit 102, which in the preferred embodiment is a nasal oxygen catheter. However, intake unit 102 may be a oxygen mask, funnel or the like for delivering gas to the patient.

There is illustrated in FIG. 4 a bottom perspective view of the exterior of the present invention. Referring to FIG. 4, attachable housing 12 has conduit aperture 20 for allowing extension of flexible flow conduit 50. Conduit 50 is extended through aperture 20 during the extension state. Conduit 50 is uncoiled as the patient moves around a large area away from stationary gas supply 28 and device 10. When the patient moves toward device 10, the extraneous conduit 50 is recoiled into housing 12 through aperture 20. Attachable housing 12 consists of attachment casing member 14 and inlet casing member 16 which are mated to each other. Inlet flow conduit 22 enters housing 12 at inlet aperture 18, not shown.

There is illustrated in FIG. 5 a side perspective view of the interior of the present invention. Referring to FIG. 5, in the interior of housing 12 is gear reel 62 which acts as a boundary for flexible flow conduit 50. Gear catch lever 68 and gear compression spring 70 are attached to the exterior face of gear reel 62, on the opposite face from conduit 50. Spring 70 is attached to gear catch lever 68 which is engaged with half gear 66 which is mounted on central swivel shaft 30, not shown. During the extension state of conduit 50, lever 68 is engaged with half gear 66. During the retraction state of conduit 50, lever 68 is disengaged from gear 66. Conduit 50 is coupled at outlet end 84 to intake unit 102, allowing for flow communication between conduit 50 and intake unit 102. In the preferred embodiment, intake unit 102 is a nasal catheter which delivers oxygen to the patient through the patient's nostrils.

Figure 7:
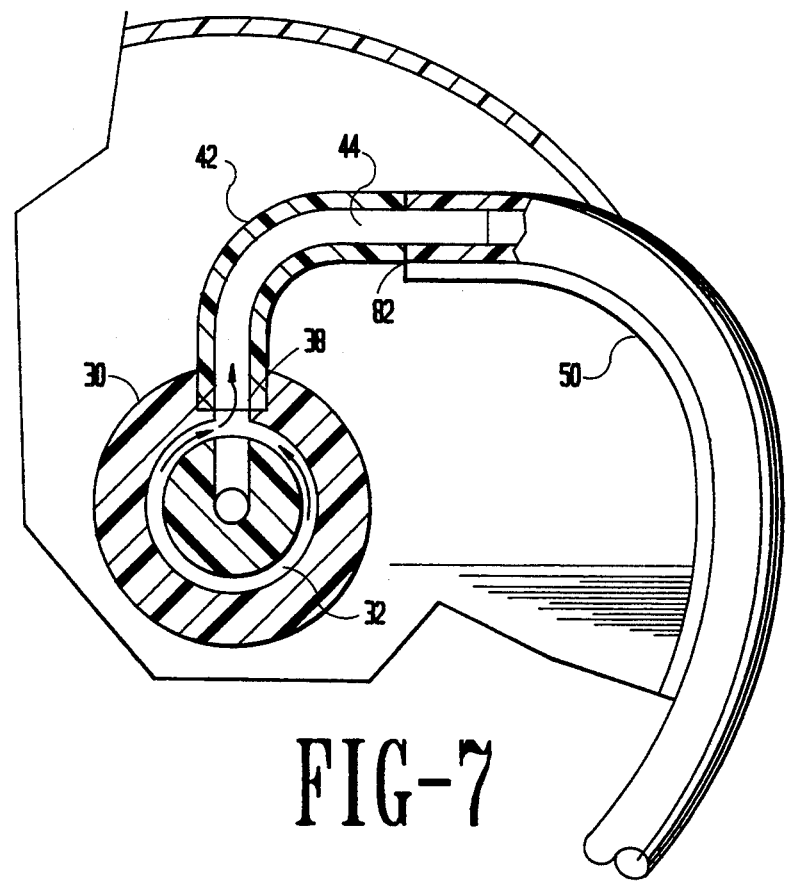
FIG. 7 is a drawing illustrating a side perspective view of the interior of the present invention.

There is illustrated in FIG. 6 a side perspective view of the interior of the present invention. There is illustrated in FIG. 7 a side perspective view of the interior of the present invention. Referring to FIGS. 6 and 7, flexible flow conduit 50 is wound in a coil around cylindrical portion 54 of spring reel 52. Inlet end 82 of conduit 50 is attached to extension unit 42 allowing for flow communication between extension passage way 44 and conduit 50. Extension unit 42 is attached to central swivel shaft 30 at middle aperture 38 allowing for flow communication between extension passageway 44 and central passageway 32. In this manner, gas, such as oxygen, is transferred from the central passageway 32 to extension passageway 44 to conduit 50. Conduit 50 is wound around cylindrical portion 54 in such a manner as to prevent tangling and constriction of conduit 50. Also, the one hundred eighty degree movement of extension unit 42 prevents tangling and constriction of conduit 50 during the retraction state. In the preferred embodiment, flexible flow conduit 50 is approximately fifteen meters in length, allowing the patient undergoing oxygen therapy to freely move about an approximately seven hundred square meter area. Device 10 may also be utilized in the deliver of nitrous oxide or other medicinal gases delivered to a patient.

Maintenance of tubing used in oxygen therapy, or other medicinal gas therapy, must be performed on a regular basis in order to prevent contamination of the tubing, which might prove fatal to a patient undergoing gas therapy. The tubing is removed from use in oxygen therapy, then cleansed and sterilized by a servicing company. The tubing is then returned for further use in oxygen therapy, or any other medicinal gas therapy. In a hospital where tens, or even hundreds of tubing must be serviced, the present invention allows for facilitated servicing of the tubing which results in significant time saving on behalf of the servicing company. During servicing, intake unit 102 is uncoupled from outlet end 84. Then, conduit 50 is recoiled into housing 12, and is in its coil state, wound around cylindrical portion 54 of spring reel 52. Casing member 14 is removed through unbolting plurality of countersunk bolts 17, which exposes the interior of housing 12. Gear reel 62 is uncoupled from spring reel 52 through plurality of couplings 53. Once gear reel 52 is removed from housing 12, conduit 50 is exposed and can be easily uncoupled from extension unit 42 at inlet end 82. Conduit 50 is then removed from housing 12, in its coiled state. A new conduit 50 in its coiled state is placed into housing 12 around cylindrical portion 54 and coupled to extension unit 42 at conduit's 50 inlet end 82. Gear reel 62 is then recoupled to spring reel 52 through plurality of couplings 53. Casing member 14 is then reconnected to casing member 16 through plurality of countersunk bolts 17. If inlet conduit 22 also needs servicing, then conduit 22 can be uncoupled from shaft 30 and gas supply 28, and a new conduit 22 installed. The intake unit 102 is then recoupled at outlet end 84 of conduit 50 and the device 10 is again ready for use in oxygen therapy, or any other form of medicinal gas therapy.

In operation, a patient undergoing oxygen therapy, or any other medicinal gas therapy, is in virtually constant need of oxygen. Prior to the present invention, the patient needed to be in close proximity to the stationary gas supply 28 which limited their movement. Utilizing the present invention, inlet conduit 22 is coupled at exterior end 26 to a releasing valve of stationary gas supply 28. Inlet conduit 22 is then placed therethrough inlet aperture 18 and coupled to spring end 36 of central swivel shaft 30 at its interior end 24. Housing 12 is attached to stationary gas supply 28 or some other stationary object through attachment means 19. Patient gas intake unit 102 is coupled to outlet end 84 of conduit 50. In the preferred embodiment, intake unit 102 is a nasal catheter which is placed about the patient's head with the nasal tubing insert into the patient's nostrils. An alligator clip may be used to attach conduit 50 to a patient's robe in order to prevent uncoupling of intake unit 102 and conduit 50 due to movement by the patient. Oxygen, or any other medicinal gas, is transferred from supply gas unit 28, through inlet flow conduit 22, through central passageway 32, through extension passageway 44, through flexible flow conduit 50, to intake unit 102 and to the patient. As the patient moves about their hospital room and beyond, conduit 50 is extended from housing 12. During the extension state, spring reel 52 and gear reel 62 are rotating about shaft 30 in a first direction. Also during the extension state, tension spring 58 is being tightened around central shaft 30, and gear catch lever 68 is engaged with half gear 66. If the patient moves toward device 10, or if there is excess conduit about the floor of the patient's room, the patient only need slightly tug conduit 50 which retracts any excess conduit 50 into housing 12. During the retraction state, tension spring 58 is slowly released, and gear catch lever 68 is disengaged from half gear 66. In this manner, the present invention allows for greater movement on behalf of the patient, and easy retraction of any excess tubing preventing tangling and constriction of the tubing, and also preventing condensation of the tubing.

While the preferred embodiment of the invention has been shown and described, it will be apparent to those skilled in this art that various modifications may be made in the embodiment without departing from the spirit of the present invention. Therefore, the embodiments of the invention in which an exclusive property or privilege is claimed are defined as follows:

What is claimed is:

1. A retractable tubing reel device, utilized in conjunction with a stationary gas supply and a patient intake unit such as a nasal catheter, the retractable tubing reel device comprising:

an attachable housing consisting of a attachment casing member and an inlet casing member, the attachment casing member and inlet casing member essentially symmetrical in shape and mated to each other, the attachment casing member having means for attachment to a base unit, the inlet casing member having an inlet aperture, the attachable housing having a conduit aperture;

an inlet flow conduit having a exterior end and an interior end, the inlet flow conduit therethrough said inlet aperture and in flow communication with a stationary gas supply at the exterior end, and the interior end inside said attachable housing, the inlet flow conduit delivering gas from the stationary gas supply to a retractable tubing reel device;

a central swivel shaft enclosed within and at a horizontal axis across said attachable housing, the central swivel shaft essentially cylindrical having a gear end and a spring end opposite each other, the central swivel shaft having a central passageway for flow of gas, in flow communication with said inlet flow conduit at the spring end, the central swivel shaft having a spring catch on a perimeter of the central swivel shaft near the spring end, the central swivel shaft stationary about the horizontal axis of said attachable housing;

an extension unit having a swivel end and a conduit end, attached perpendicular to said central swivel shaft at the swivel end, the extension unit having an extension passageway therethrough, in flow communication with said central passageway;

a flexible flow conduit having an inlet end and an outlet end, attached to said extension unit at the inlet end, and through said conduit aperture of said attachable housing to the patient gas intake unit at the outlet end, the flexible flow conduit in flow communication with said extension passageway and the patient gas intake unit, the flexible flow conduit wound in a coil inside said attachable housing during a coil state, the flexible flow conduit extended beyond said attachable housing during an extension state, the flexible flow conduit being rewound inside said attachable housing during a retraction state, the flexible flow conduit delivering gas flowing through said extension passageway to the patient gas intake unit;

a gear assembly enclosed within said attachable housing, having a gear reel, a gear catch lever, a half gear, and a gear compression spring, the gear reel circular in shape having a central aperture for engagement with said gear end of said central swivel shaft, the gear reel mounted on and rotating about said central swivel shaft and forming a first boundary for said flexible flow conduit, the gear catch lever connected to the gear reel, a half gear mounted to said gear end of said central swivel shaft, the half gear engaging the gear catch lever as said flexible flow conduit is extended from said attachable housing during said extension state, the half gear disengaging the gear catch lever during said retraction state; and a spring assembly enclosed within said attachable housing, having a spring reel and a tension spring, the spring reel having a flat circular portion and a cylindrical portion perpendicular to the circular portion, the cylindrical portion attached to said gear reel through a plurality of reel couplings, the spring reel having a central cavity, said central swivel shaft extended therethrough and engaged with said spring reel at said spring end of said central swivel shaft, the tension spring, eccentric to said central swivel shaft and enclosed within the cylindrical portion of said spring reel, the tension spring connected to said central swivel shaft through said spring catch and to the cylindrical portion, said flexible flow conduit wound around the cylindrical portion of the spring reel, the flat circular portion of the spring reel forming a second boundary for said flexible flow conduit, said spring reel rotating in a first direction when said flexible flow conduit is being extended and rotating in an opposite direction when said flexible flow conduit is being retracted, said gear reel rotating reciprocally with the spring reel;

whereby a patient, under gas therapy in which a gas must constantly be supplied to the patient, may have the freedom to move about a large area from the stationary gas supply unit, through extending said flexible flow conduit beyond said attachable housing, the flexible flow conduit retractable to prevent tangling and constriction of the flexible flow conduit, gas flowing from the stationary gas supply unit through said inlet flow conduit, through said central passageway to said extension passageway to said flexible flow conduit, to the patient gas intake unit and to the patient.

2. The retractable tubing reel device according to claim 1 wherein said flexible flow conduit is a plastic tubing.

3. The retractable tubing reel device according to claim 1 wherein said attachable housing is composed of hard plastic material.

4. The retractable tubing reel device according to claim 1 wherein said inlet flow conduit is plastic tubing.

5. The retractable tubing reel device according to claim 1 wherein said attachment means is velcro straps, and wherein said attachment casing member is connected to said inlet casing member through a plurality of bolts.

6. The retractable tubing reel device according to claim 1 wherein said flexible flow conduit is composed of a material conducive to the deliver of gases.

7. The retractable tubing reel device according to claim 1 wherein said flexible flow conduit is of a predetermined length.

8. The retractable tubing reel device according to claim 1 wherein the gas supplied to the patient is oxygen.

9. The retractable tubing reel device according to claim 1 wherein:

said coil state is when said flexible flow conduit is completely wound around said cylindrical portion of said spring reel and said tension spring is substantially relaxed;

said extension state is when any portion of said flexible flow conduit is extended beyond said attachable housing and said tension spring is tightened; and, said retraction state is when said flexible flow conduit is being recoiled into said attachable housing and rewound around said cylindrical portion of said spring reel and said tension spring is being untightened.

10. The retractable tubing reel device according to claim 1 wherein the gas supplied to the patient is nitrous oxide.

11. A retractable tubing reel device, utilized in conjunction with a stationary oxygen supply tank and a nasal oxygen catheter, the retractable tubing reel device comprising:

an attachable housing consisting of a attachment casing member and an inlet casing member, the attachment casing member and inlet casing member essentially symmetrical in shape and mated to each other, the attachment casing member having means for attachment to a base unit, the inlet casing member having an inlet aperture, the attachable housing having a conduit aperture;

an inlet flow conduit having a exterior end and an interior end, the inlet flow conduit therethrough said inlet aperture and in flow communication with the oxygen supply tank at the exterior end, and the interior end inside said attachable housing, the inlet flow conduit delivering oxygen from the stationary oxygen supply tank to a retractable tubing reel device;

a central swivel shaft enclosed within and at a horizontal axis across said attachable housing, the central swivel shaft essentially cylindrical having a gear end and a spring end opposite each other, the central swivel shaft having a central passageway for flow of oxygen, in flow communication with said inlet flow conduit at the spring end, the central swivel shaft having a spring catch on a perimeter of the central swivel shaft near the spring end, the central swivel shaft stationary about the horizontal axis of said attachable housing;

an extension unit having a swivel end and a conduit end, attached perpendicular to said central swivel shaft at the swivel end, the extension unit having an extension passageway therethrough, in flow communication with said central passageway;

a flexible flow conduit having an inlet end and an outlet end, attached to said conduit end of said extension unit at the inlet end and through said conduit aperture of said attachable housing to the nasal oxygen catheter at the outlet end, the flexible flow conduit in flow communication with said extension passageway and the nasal oxygen catheter, the flexible flow conduit wound in a coil inside said attachable housing during a coil state, the flexible flow conduit extended beyond said attachable housing during an extension state, the flexible flow conduit being rewound inside said attachable housing during a retraction state, the flexible flow conduit transferring oxygen flowing through said extension passageway to the nasal oxygen catheter;

a gear assembly enclosed within said attachable housing, having a gear reel, a gear catch lever, a half gear, and a gear compression spring, the gear reel circular in shape having a central aperture for engagement with said gear end of said central swivel shaft, the gear reel mounted on and rotating about said central swivel shaft and forming a first boundary for said flexible flow conduit, the gear catch lever connected to the gear reel, a half gear mounted to said gear end of said central swivel shaft, the half gear engaging the gear catch lever as said flexible flow conduit is extended from said attachable housing during said extension state, the half gear disengaging the gear catch lever during said retraction state; and a spring assembly enclosed within said attachable housing, having a spring reel and a tension spring, the spring reel having a flat circular portion and a cylindrical portion perpendicular to the circular portion, the cylindrical portion attached to said gear reel through a plurality of reel couplings, the spring reel having a central cavity, said central swivel shaft extended therethrough and engaged with said spring reel at said spring end of said central swivel shaft, the tension spring, eccentric to said central swivel shaft and enclosed within the cylindrical portion of said spring reel, the tension spring connected to said central swivel shaft through said spring catch and to the cylindrical portion, the tension spring tightening during said extension state and untightening during said retraction state, said flexible flow conduit wound around the cylindrical portion of the spring reel, the flat circular portion of the spring reel forming a second boundary for said flexible flow conduit, said spring reel rotating in a first direction when said flexible flow conduit is being extended and rotating in an opposite direction when said flexible flow conduit is being retracted, said gear reel connected to the spring reel through a plurality of couplings;

whereby a patient, under oxygen therapy in which oxygen must constantly be supplied to the patient, may have the freedom to move about a large area from the stationary oxygen supply tank, through extending said flexible flow conduit beyond said attachable housing, the flexible flow conduit retractable to prevent tangling and constriction of the flexible flow conduit, oxygen is transferred from the stationary oxygen supply tank through said inlet flow conduit, through said central passageway to said extension passageway to said flexible flow conduit, to the patient gas intake unit and to the patient.

12. The retractable tubing reel device according to claim 11 wherein said flexible flow conduit is a plastic tubing.

13. The retractable tubing reel device according to claim 11 wherein said attachable housing is composed of a hard plastic material.

14. The retractable tubing reel device according to claim 11 wherein said inlet flow conduit is plastic tubing.

15. The retractable tubing reel device according to claim 11 wherein said attachment means is velcro straps and wherein said attachment casing member is connected to said inlet casing member through a plurality of bolts.

16. The retractable tubing reel device according to claim 11 wherein said flexible flow conduit is composed of a material conducive to the transfer of oxygen.

17. The retractable tubing reel device according to claim 11 wherein said flexible flow conduit is of a predetermined length.

18. The retractable tubing reel device according to claim 11 wherein:

said coil state is when said flexible flow conduit is completely wound around said cylindrical portion of said spring reel and said tension spring is substantially relaxed;

said extension state is when any portion of said flexible flow conduit is extended beyond said attachable housing and said tension spring is tightened; and, said retraction state is when said flexible flow conduit is being recoiled into said attachable housing and rewound around said cylindrical portion of said spring reel and said tension spring is being untightened.

* * * * *